US009877840B2

(12) United States Patent
Woodburn, Sr. et al.

(10) Patent No.: US 9,877,840 B2
(45) Date of Patent: *Jan. 30, 2018

(54) ADJUSTABLE INTERVERTEBRAL IMPLANT

(71) Applicant: DePuy Synthes Products, Inc., Raynham, MA (US)

(72) Inventors: William N. Woodburn, Sr., Mantua, NJ (US); Tom Pepe, Turnersville, NJ (US); William McDonough, Collegeville, PA (US); Douglas S. Kephart, Glen Mills, PA (US); David E. Evans, Downingtown, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/012,529

(22) Filed: Aug. 28, 2013

(65) Prior Publication Data
US 2014/0067072 A1 Mar. 6, 2014

Related U.S. Application Data

(63) Continuation of application No. 13/061,388, filed as application No. PCT/US2008/075251 on Sep. 4, 2008, now Pat. No. 8,540,770.

(51) Int. Cl.
*A61F 2/44* (2006.01)
*A61F 2/46* (2006.01)
(Continued)

(52) U.S. Cl.
CPC .............. *A61F 2/442* (2013.01); *A61F 2/44* (2013.01); *A61F 2/4611* (2013.01);
(Continued)

(58) Field of Classification Search
CPC .......... A61F 2/44; A61F 2/442; A61F 2/4425; A61F 2/4455; A61F 2/446; A61F 2/4465;
(Continued)

(56) References Cited

U.S. PATENT DOCUMENTS 4,553,273 A 11/1985 Wu
4,554,914 A 11/1985 Kapp et al.
(Continued)

FOREIGN PATENT DOCUMENTS

AU 772396 B2 4/2004
CA 2317095 A1 3/2001
(Continued)

OTHER PUBLICATIONS

International Preliminary Report on Patentability and Written Opinion, dated Mar. 8, 2011, in connection with International Application No. PCT/US2008/075251.
(Continued)

*Primary Examiner* — Christian Sevilla
*Assistant Examiner* — Tracy Kamikawa
(74) *Attorney, Agent, or Firm* — Meunier Carlin & Curfman LLC

(57) ABSTRACT

An adjustable intervertebral implant for implantation into a patient's spine in-between first and second adjacent or neighboring vertebrae. The implant may include one or more of the following features: (i) inner and outer members coupled by a radiographically imagable expansion ring, (ii) detachable endplates coupled to the implant via a polygonal press-fit coupling interface that accommodate a range of lordotic endplates to be applied to the implant using any surgical approach, (iii) an interference pre-loaded set screw for selectively locking the height of the construct, (iv) a radiographically imagable marker for determining the
(Continued)

expansion of the implant, and (v) an asymmetric thread coupling between the expansion ring and the inner member.

20 Claims, 12 Drawing Sheets

(51) Int. Cl.
*A61F 2/30* (2006.01)
*A61F 2/28* (2006.01)

(52) U.S. Cl.
CPC ... *A61F 2/30744* (2013.01); *A61F 2002/2835* (2013.01); *A61F 2002/305* (2013.01); *A61F 2002/3008* (2013.01); *A61F 2002/3055* (2013.01); *A61F 2002/30133* (2013.01); *A61F 2002/30237* (2013.01); *A61F 2002/30369* (2013.01); *A61F 2002/30383* (2013.01); *A61F 2002/30405* (2013.01); *A61F 2002/30492* (2013.01); *A61F 2002/30495* (2013.01); *A61F 2002/30507* (2013.01); *A61F 2002/30523* (2013.01); *A61F 2002/30594* (2013.01); *A61F 2002/30601* (2013.01); *A61F 2002/30604* (2013.01); *A61F 2002/30616* (2013.01); *A61F 2002/30787* (2013.01); *A61F 2002/30794* (2013.01); *A61F 2002/30841* (2013.01); *A61F 2002/4475* (2013.01); *A61F 2002/4628* (2013.01); *A61F 2220/0025* (2013.01); *A61F 2220/0033* (2013.01); *A61F 2230/0015* (2013.01); *A61F 2230/0069* (2013.01); *A61F 2250/0098* (2013.01); *A61F 2310/00017* (2013.01); *A61F 2310/00023* (2013.01); *A61F 2310/00179* (2013.01)

(58) Field of Classification Search
CPC .......... A61F 2/447; A61F 2/46; A61F 2/4603; A61F 2/4611; A61F 2002/443; A61F 2002/4475; A61F 2002/30579; Y10T 403/32467; Y10T 403/32491; Y10T 403/32516; Y10T 403/32524
USPC .............. 623/17.11–17.16; 403/109.1, 109.4
See application file for complete search history.

(56) References Cited

U.S. PATENT DOCUMENTS

| | | | |
|---|---|---|---|
| 4,657,550 A * | 4/1987 | Daher | 623/17.11 |
| 5,236,460 A | 8/1993 | Barber et al. | |
| 5,290,312 A | 3/1994 | Kojimoto et al. | |
| 5,489,308 A | 2/1996 | Kuslich et al. | |
| 5,571,192 A | 11/1996 | Schonhoffer | |
| 5,702,453 A | 12/1997 | Rabbe et al. | |
| 5,702,455 A | 12/1997 | Saggar | |
| 5,723,013 A | 3/1998 | Jeanson et al. | |
| 5,776,197 A | 7/1998 | Rabbe et al. | |
| 5,776,198 A | 7/1998 | Rabbe et al. | |
| 5,916,267 A | 6/1999 | Tienboon | |
| 5,989,290 A * | 11/1999 | Biedermann et al. | 623/17.11 |
| 6,015,436 A | 1/2000 | Schönhöffer | |
| 6,086,613 A | 7/2000 | Camino et al. | |
| 6,190,413 B1 | 2/2001 | Sutcliffe et al. | |
| 6,193,755 B1 | 2/2001 | Metz-Stavenhagen et al. | |
| 6,193,756 B1 | 2/2001 | Studer et al. | |
| 6,200,348 B1 | 3/2001 | Biedermann et al. | |
| 6,616,695 B1 | 9/2003 | Crozet et al. | |
| 6,752,832 B2 | 6/2004 | Neumann et al. | |
| 6,776,798 B2 | 8/2004 | Camino et al. | |
| 6,866,682 B1 | 3/2005 | An et al. | |
| 6,974,480 B2 * | 12/2005 | Messerli et al. | 623/17.16 |
| 6,991,653 B2 | 1/2006 | White et al. | |
| 7,608,078 B2 | 10/2009 | Berry et al. | |
| 7,648,529 B2 | 1/2010 | An et al. | |
| 7,887,594 B2 | 2/2011 | Berry et al. | |
| 7,909,870 B2 | 3/2011 | Kraus | |
| 8,142,441 B2 | 3/2012 | Refai et al. | |
| 8,182,537 B2 | 5/2012 | Refai et al. | |
| 8,540,770 B2 | 9/2013 | Evans et al. | |
| 8,591,587 B2 | 11/2013 | Ebersole et al. | |
| 8,690,950 B2 | 4/2014 | Ebersole et al. | |
| 2003/0045877 A1 * | 3/2003 | Yeh | 606/61 |
| 2004/0210312 A1 | 10/2004 | Neumann et al. | |
| 2005/0071007 A1 | 3/2005 | Malek | |
| 2005/0113921 A1 | 5/2005 | An et al. | |
| 2005/0192578 A1 * | 9/2005 | Horst | 606/69 |
| 2006/0100710 A1 * | 5/2006 | Gutlin et al. | 623/17.15 |
| 2006/0241762 A1 | 10/2006 | Kraus | |
| 2006/0241770 A1 | 10/2006 | Rhoda et al. | |
| 2008/0215151 A1 * | 9/2008 | Kohm et al. | 623/17.11 |

FOREIGN PATENT DOCUMENTS

| | | |
|---|---|---|
| DE | 3729600 A1 | 3/1989 |
| DE | 3741487 A1 | 6/1989 |
| DE | 4012622 C1 | 7/1991 |
| DE | 19604246 A1 | 8/1996 |
| DE | 19509317 | 9/1996 |
| DE | 19622827 | 12/1997 |
| DE | 20320974 U1 | 8/2005 |
| DE | 10357926 B3 | 9/2005 |
| EP | 0490159 A1 | 6/1992 |
| EP | 0904751 A1 | 3/1999 |
| EP | 977528 A1 | 2/2000 |
| EP | 1080703 | 7/2001 |
| EP | 1501453 A1 | 2/2005 |
| EP | 1694257 A2 | 8/2006 |
| EP | 2343030 | 7/2011 |
| JP | 08-224265 A | 9/1996 |
| JP | 08-266564 A | 10/1996 |
| JP | 2000197652 A | 7/2000 |
| JP | 2000210315 A | 8/2000 |
| WO | 1997047258 A1 | 12/1997 |
| WO | 1998048738 A1 | 11/1998 |
| WO | 1999038462 A1 | 8/1999 |
| WO | 1999063913 A2 | 12/1999 |
| WO | 2000035388 A1 | 6/2000 |
| WO | 2005055887 A2 | 6/2005 |
| WO | 2008/112923 | 9/2008 |
| WO | 2010/027359 | 3/2010 |
| WO | 2010/031365 | 3/2010 |
| WO | 2011/053583 | 5/2011 |

OTHER PUBLICATIONS

International Search Report, dated Jun. 5, 2009, in connection with International Application No. PCT/US2008/075251.

* cited by examiner

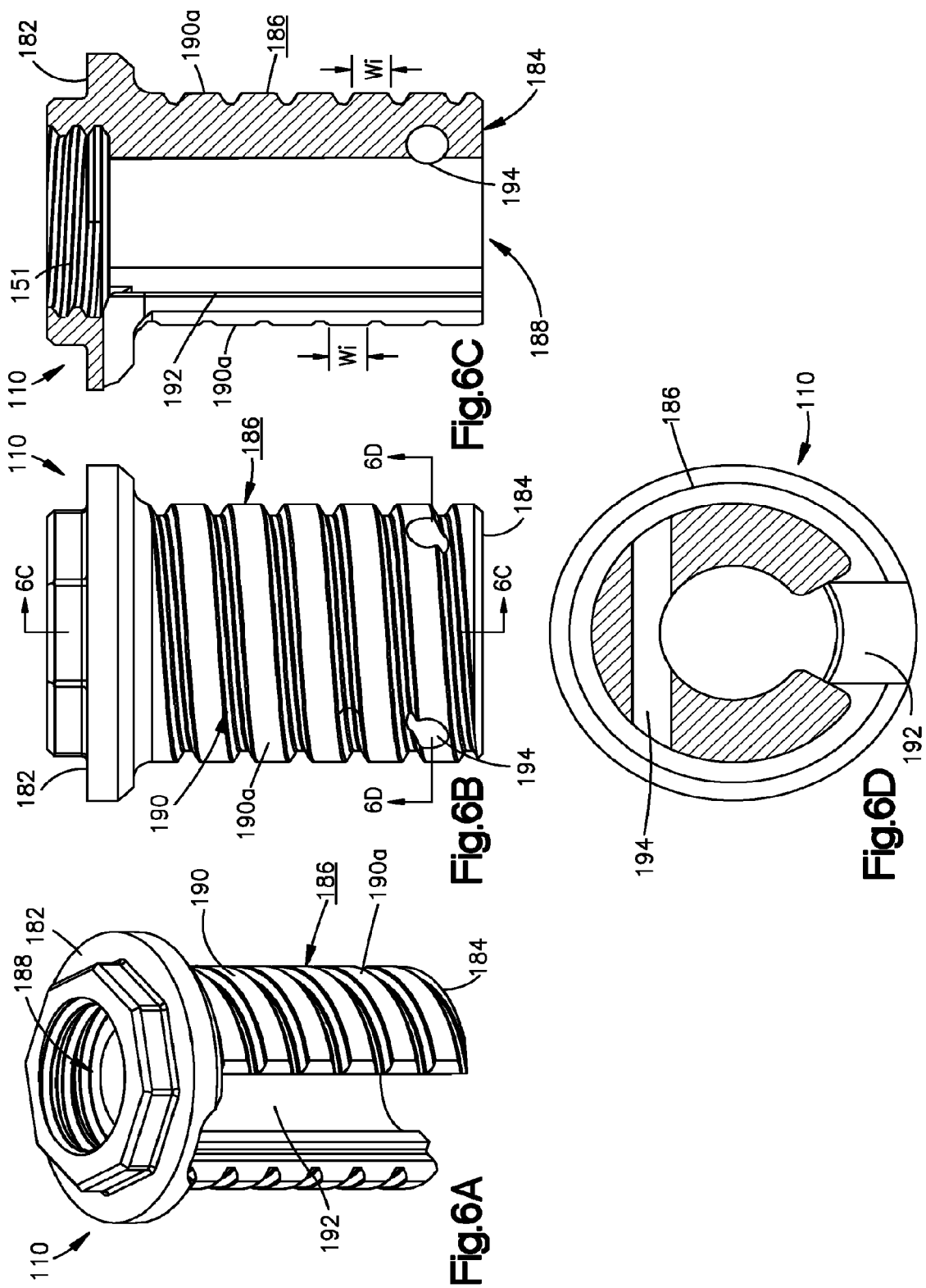

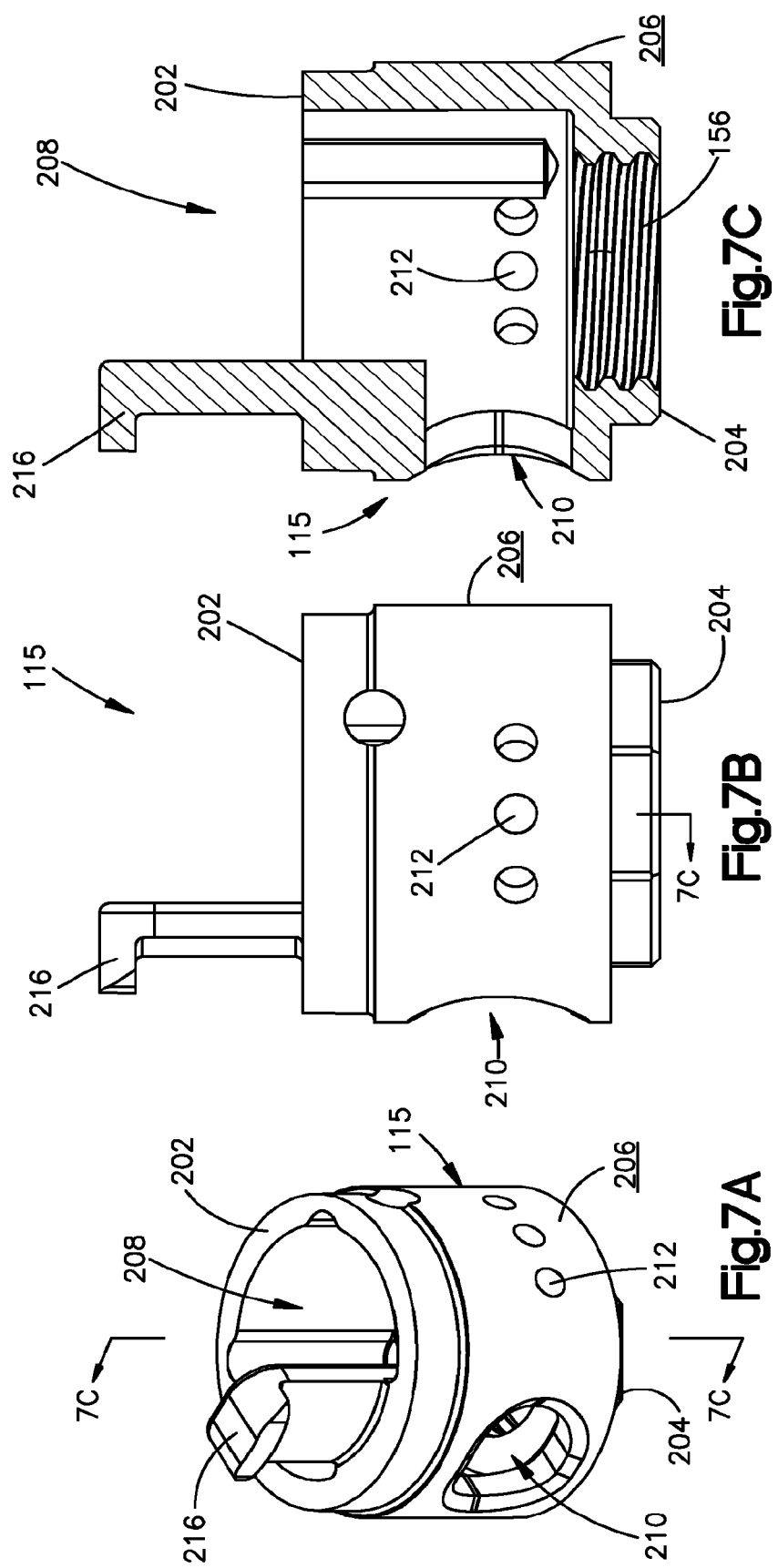

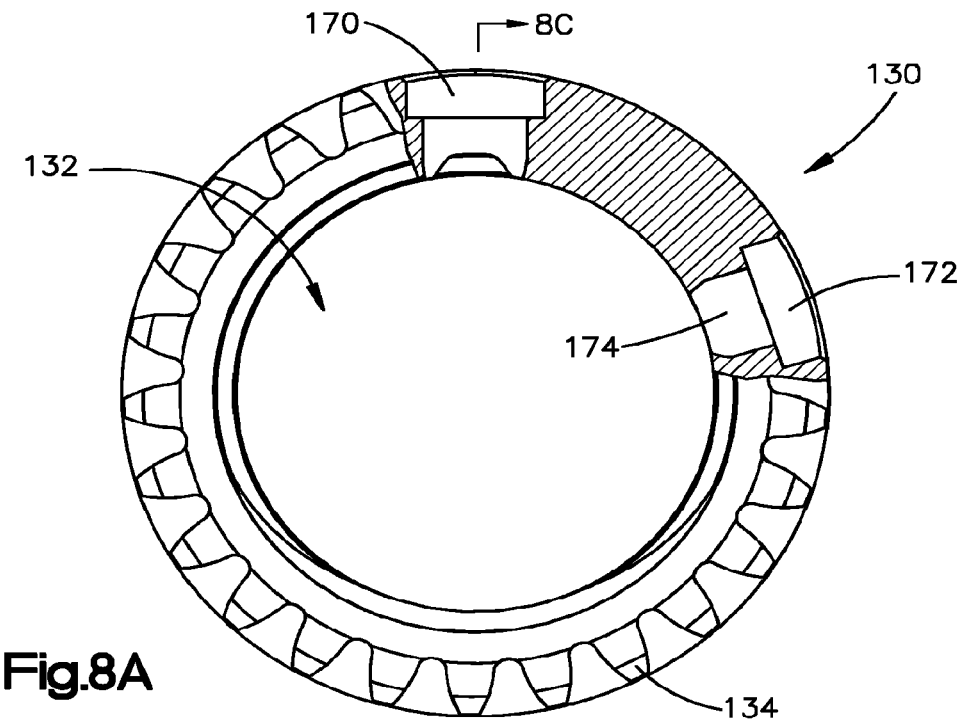
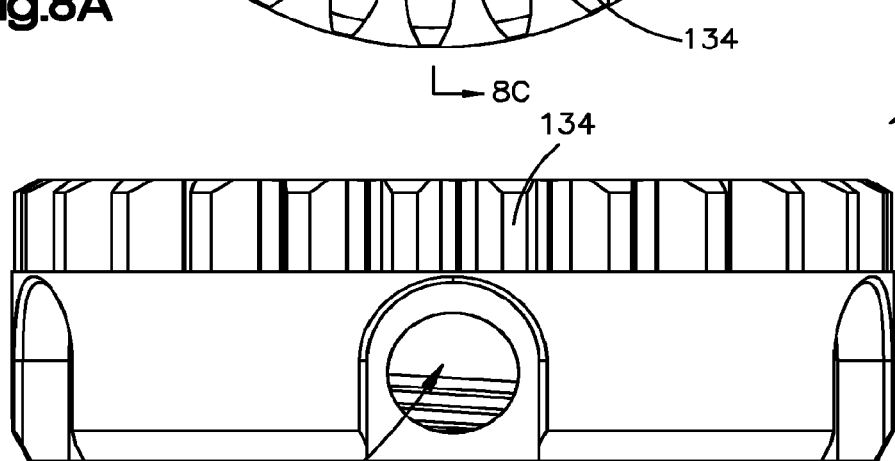
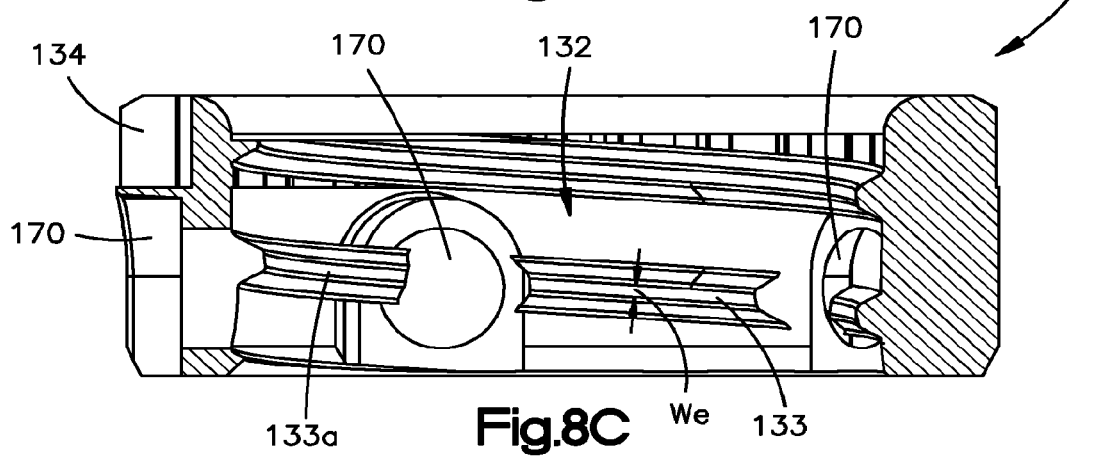

ADJUSTABLE INTERVERTEBRAL IMPLANT

RELATED APPLICATIONS

This application is a continuation of U.S. application Ser. No. 13/061,388, filed Feb. 28, 2011, entitled "ADJUSTABLE INTERVERTEBRAL IMPLANT" which was a National Stage of International Application No. PCT/2008/075251, filed Sep. 4, 2008, the entire disclosures of which is hereby incorporated by reference.

BACKGROUND OF THE INVENTION

The present invention relates to an intervertebral implant, and, more particularly, to an adjustable height intervertebral implant that preferably enables the user to adjust the height of the implant.

Degenerative disc disease or degeneration of a vertebral body often results in a loss of disc height, which in turn can cause, inter alia, facet and nerve impingement. One standard of care is to replace the damaged intervertebral disc with an intervertebral implant or a damaged portion or an entire vertebral body with an intervertebral implant. That is, after removal of a damaged intervertebral disk, a damaged nucleus pulpous of an intervertebral disk or a damaged portion or entire vertebral body, an intervertebral implant is inserted into the intervertebral space of two neighboring vertebral bodies or into the space created by removal of portions of or the entire vertebral body. Preferably the intervertebral implant restores the spine as much as possible to a natural state, i.e. to restore the original height of the intervertebral disk and thus the original distance between the two neighboring or adjacent vertebral bodies or vertebral bodies in various levels of the spine.

BRIEF SUMMARY OF THE INVENTION

The present invention is directed to an adjustable intervertebral implant for insertion between first and second vertebral bodies. The implant may include a first member, a second member, and an expansion ring operatively associated with the first and second members, the ring includes one or more threads for engaging one or more threads formed on the outer surface of the first member so that rotation of the ring causes the first member to axially move or translate with respect to the second member. The first member may be slightly smaller than the second member so that the first member is received at least partially within the second member.

BRIEF DESCRIPTION OF THE SEVERAL VIEWS OF THE DRAWINGS

The foregoing summary, as well as the following detailed description of a preferred embodiment of the adjustable intervertebral implant or device of the present application, will be better understood when read in conjunction with the appended drawings. For the purposes of illustrating the corpectomy implant of the present application, there is shown in the drawings a preferred embodiment of the implant and tooling for implanting same. It should be understood, however, that the application is not limited to the precise arrangements and instrumentalities shown. In the drawings:

FIG. 6A illustrates a top perspective view of an inner member of the adjustable intervertebral implant of FIG. 1;

FIG. 6B illustrates a rear elevational view of the inner member of FIG. 6A;

FIG. 6C illustrates a cross-sectional view of the inner member of FIG. 6A, taken along line 6C-6C of FIG. 6B;

FIG. 6D illustrates a cross-sectional view if the inner member of FIG. 6A, taken along line 6D-6D of FIG. 6B;

FIG. 7A illustrates a top perspective view of an outer member of the adjustable intervertebral implant of FIG. 1;

FIG. 7B illustrates a side elevational view of the outer member of FIG. 7A;

FIG. 7C illustrates a cross-sectional view of the outer member of FIG. 7A, taken along line 7C-7C of FIG. 7A;

FIG. 8A illustrates a bottom plan view of an expansion ring member of the adjustable intervertebral implant of FIG. 1;

FIG. 8B illustrates a side elevational view of the expansion ring member of FIG. 8A;

FIG. 8C illustrates a cross-sectional view of the expansion ring member of FIG. 8A, taken along line 8C-8C of FIG. 8A;

DETAILED DESCRIPTION OF THE INVENTION

Figure 1:
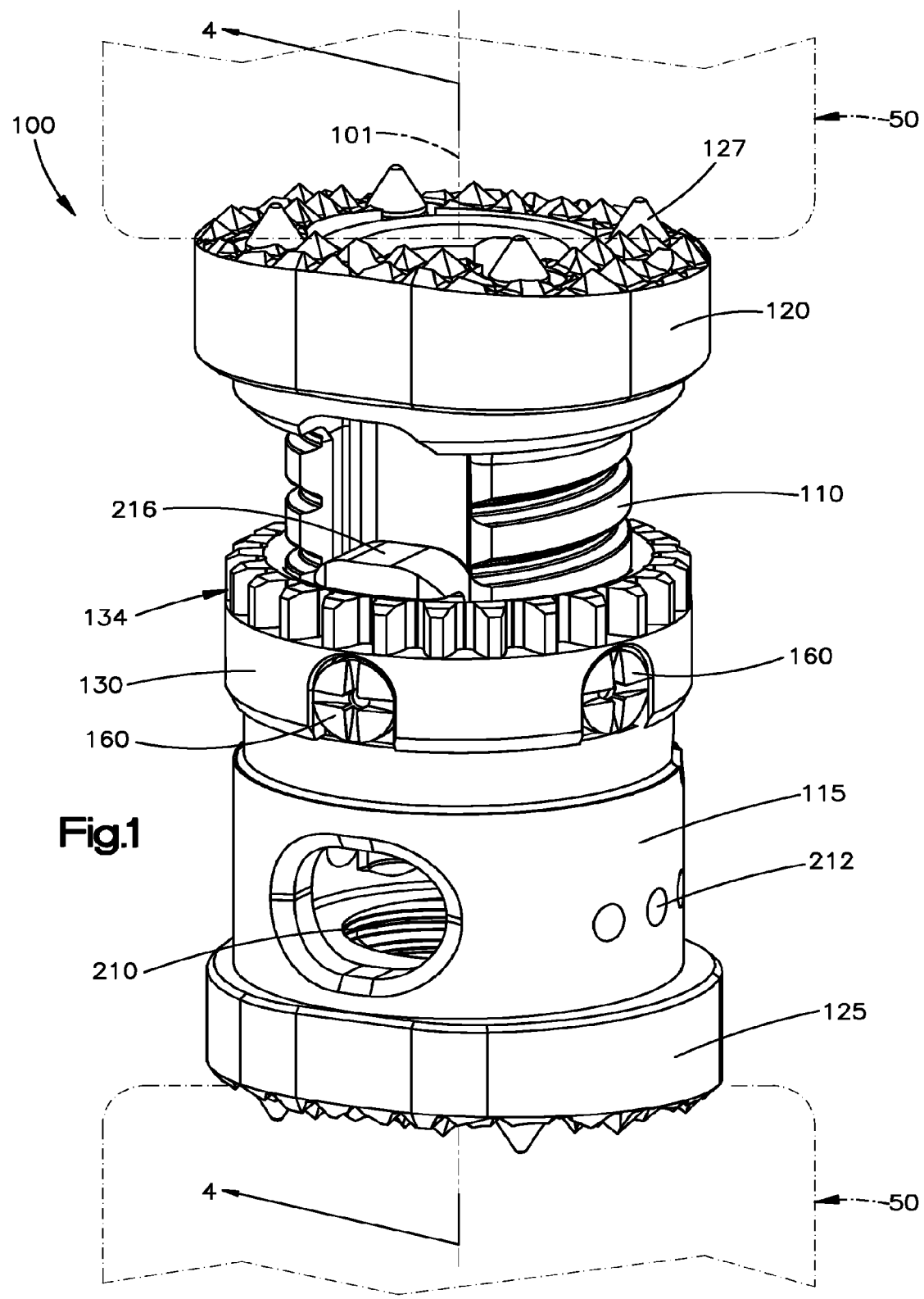
FIG. 1 illustrates a front perspective view of an adjustable intervertebral implant in accordance with a preferred embodiment of the present invention.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the adjustable intervertebral implant, the insertion tool and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

An exemplary embodiment will now be described with reference to the drawings. In general, such embodiments relate to an intervertebral implant, by way of non-limiting example, an adjustable intervertebral implant for implantation into a patient's spine in-between first and second adjacent or neighboring vertebrae. If used as a corpectomy device, the intervertebral implant will be able to perform single or multiple level operations, i.e., removal of one or more than one vertebra and/or portions of vertebra. An adjustable intervertebral implant is further disclosed in PCT International Application No. PCT/US08/56898, filed Mar. 13, 2008, entitled ADJUSTABLE INTERVERTEBRAL IMPLANT, the entire contents of which are hereby incorporated by reference.

The intervertebral implant may have alternate applications and uses to those described herein and should not be limited to the structure or uses described and illustrated herein. That is, while the intervertebral implant will be described as and may generally be used in the spine (for example, in the lumbar, thoracic or cervical regions), those skilled in the art will appreciate that the intervertebral implant may also be used in other parts of the body, and may have other applications outside of the medical device field.

Referring to FIGS. 1-8C, a preferred embodiment of an adjustable intervertebral implant 100 is configured for replacing at least a portion of a diseased or damaged vertebral body. The adjustable intervertebral implant 100 includes a first body member preferably comprising an inner member 110 having a generally tubular configuration, a second body member preferably comprising an outer member 115 having a generally tubular configuration, and an expansion ring 130, each of which are hollow so as to provide an axial bore interior to and along a longitudinal axis 101 of the adjustable intervertebral implant 100. That is, in use, the first or inner member 110 is preferably sized and configured to be slightly smaller than the second or outer member 115 so that the first member 110 is moveably disposed within the second member 115. As such, the first member 110 is generally characterized as the inner member 110 while the second member 115 is generally characterized as the outer member 115. However it should be noted that other arrangements of moveably associating the first member 110 and the second member 115 are contemplated.

As best shown in FIGS. 7A-7C, the outer member 115 preferably is a substantially hollow, tubular member having a first end 202, a second end 204, an outer surface 206 and an internal bore 208 extending substantially from the first end 202 to the second end 204. The outer member 115 preferably includes one or more relatively large bone packing openings 210 formed in the outer surface 206 thereof for providing access to the internal bore 208 such that a surgeon is able to insert bone chips or alternate graft material into the implant 100 for reasons that would be apparent to one having ordinary skill in the art. The outer member 115 also preferably includes several smaller openings 212 for permitting bone in-growth in the implanted configuration to promote fusion of adjacent vertebra 50, between which the adjustable intervertebral implant 100 is mounted in an implanted position. The intervertebral implant 100 is not limited to inclusion of the bone packing opening 210 or the smaller openings 212 and may not include openings 210, 212 therein or may include additional variably shaped openings, depending upon the specific application or configuration of the implant 100.

As best shown in FIGS. 6A-6D, the inner member 110 preferably is a substantially hollow, tubular member having a first end 182, a second end 184, an outer surface 186 and a hollow interior cavity 188. The outer surface 186 of the inner member 110 preferably includes a thread 190 formed thereon. As shown, the outer surface 186 of the inner member 110 preferably does not circumscribe three hundred sixty degrees (360°) so that the inner member 110 is preferably in the form a partial tubular member. Thus the inner member 110 preferably includes a slot 192 extending from the second end 184 thereof for reasons that will be described below. However it should be noted that the inner and outer members 110, 115 are not limited to having a tubular shape and may be alternatively shaped, such as square, elliptical or nearly any other shape that permits translation between the inner and outer members 110, 115.

Referring to FIGS. 6A-8C, the expansion ring 130 includes an inner bore 132 within which the inner member 110 is received. The expansion ring 130 is also preferably moveably coupled, more preferably rotatably attached, to the outer member 115. The expansion ring 130 may be connected to the outer member 115 by any means that enables the expansion ring 130 to be moveably coupled, preferably rotatably attached, to the outer member 115 including, but not limited to a snap-fit connection, a press-fit connection, a pin and groove arrangement, etc. Preferably, the inner and outer diameters of the expansion ring 130 and the outer member 115 are preferably similar such that the expansion ring 130 rests atop the outer member 115 and is retained with respect thereto via a tab 216. The tab 216 extends upwardly from the outer member 115 and terminates in a lip protruding substantially perpendicular to the longitudinal axis 101 of the outer member 115 such that the expansion ring 130 is slidably movable on and guided in its movement by the bottom of the tab 216 and the top of the outer member 115. The expansion ring 130 is allowed to rotate freely with respect to the outer member 115 in a released position. The inner member 110 is preferably disposed interior to the outer member 115 and is aligned with respect thereto via the slot 192 that runs parallel to the longitudinal axis 101. The slot 192 is configured to mate with the tab 216.

The interior circumference of the expansion ring 130 includes threading 133 that is configured to mate with the threading 190 formed on the outer surface 186 of the inner member 110 such that rotation of the expansion ring 130 causes the inner member 110 to translate or generally linearly move with respect to the outer member 115 along the longitudinal axis 101 of the adjustable intervertebral implant 100. That is, in use, the inner and outer members 110, 115 are preferably coaxially disposed along a common longitudinal axis 101 and are preferably slidably disposed (e.g., telescopic) with respect to one another so that the axial position of the inner member 110 is adjustable with respect to the outer member 115. Rotation of the expansion ring 130 drives a telescoping coupling between the inner and outer members 110, 115 such that, rotation of the expansion ring 130 causes the inner and outer members 110, 115 to expand or contract depending on the relative direction of the rotation.

The expansion ring 130 further preferably includes a series of teeth 134 located circumferentially around its exterior surface for engagement with a corresponding tool so that rotation of the tool, which may be either hand operated or powered, results in rotation of the expansion ring 130. In this manner, the series of teeth 134 help facilitate rotation of the expansion ring 130. Preferably, the series of teeth 134 are sized and configured to engage an insertion instrument 300, which will be described in greater detail below. When the teeth 134 are driven by the instrument 300, the expansion ring 130 is rotated resulting in the inner and outer members 110, 115 moving with respect to one another. Alternatively and/or in addition, the expansion ring 130 may be rotated manually without the aid of the teeth 134 and insertion instrument 300, or by any other means now or hereafter known.

Figure 4:
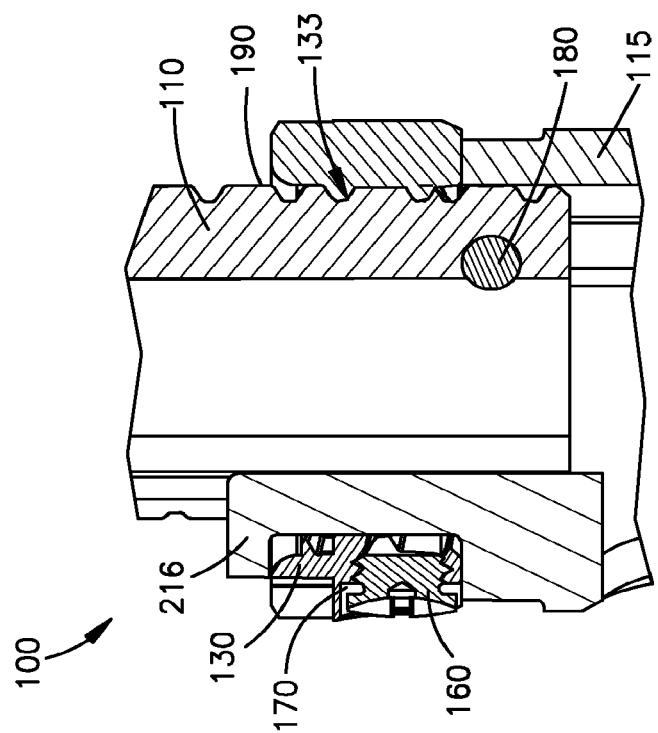
FIG. 4 illustrates a cross-sectional view of the adjustable intervertebral implant of FIG. 1, taken along line 4-4 of FIG. 1.
Figure 9:
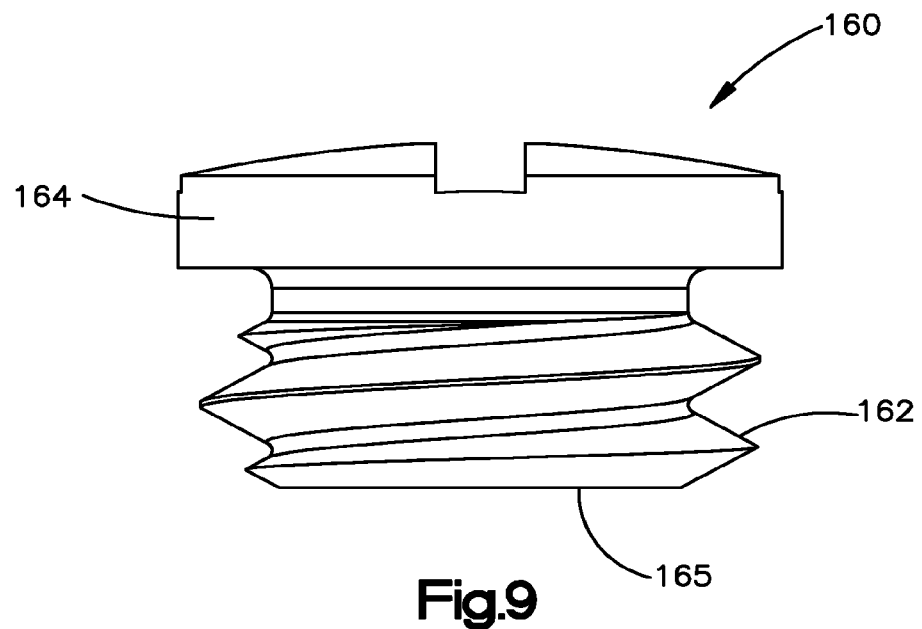
FIG. 9 illustrates a side elevational view of a screw member of the adjustable intervertebral implant of FIG. 1.

The intervertebral implant 100 may be constructed from any biocompatible material or combination of any biocompatible material known in the art including, but not limited to, stainless steel, titanium, titanium alloys, ceramics, polymers including, but not limited to polytetrafluoroethylene ("PTFE"), etc. Preferably, the inner and outer tubular members 110, 115 are formed from a radiolucent material, such as, for example, a polymer or polyetheretherketone ("PEEK"), while the expansion ring 130 is preferably formed from a metal, such as, for example, titanium or stainless steel. The threaded engagement between the interior surface of the preferably metallic expansion ring 130 and the exterior surface of the preferably polymeric or other radiolucent material inner member 110 is characterized by a threading that has an asymmetric geometry, as best shown in FIG. 4. That is, because the threads 133 formed on the expansion ring 130 are preferably made from metal they are typically stronger than the threads 190 made on the outer surface 186 of the inner member 110, which are preferably made from a polymeric material. Thus, the threads 133 made on the inner surface of the expansion ring 130 can be made thinner than the threads 190 made on the outer surface 186 of the inner member 110. Preferably, the metallic threads 133 formed on the expansion ring 130 are configured so that the strength of the metallic threads 133 is substantially similar to the strength of the thicker polymeric threads 190 formed on the outer surface 186 of the inner member 115. More specifically, preferably, a width $W_e$ of thread crests 133a that are formed on the interior surface of the metallic expansion ring 130 is thinner than a width $W_i$ of thread crests 190a that are formed the external surface of the polymer inner member 110. The mating of the thicker polymer threads 190 with the thinner metallic threads 133 provides a configuration in which more thread loading occurs over a shorter span of thread engagement when compared to standard symmetrical thread forms between atypical materials, in which the stronger material threads are as thick as the weaker material threads and which results in an increased area of threaded contact necessary to provide similar load bearing capabilities.

Figure 2:
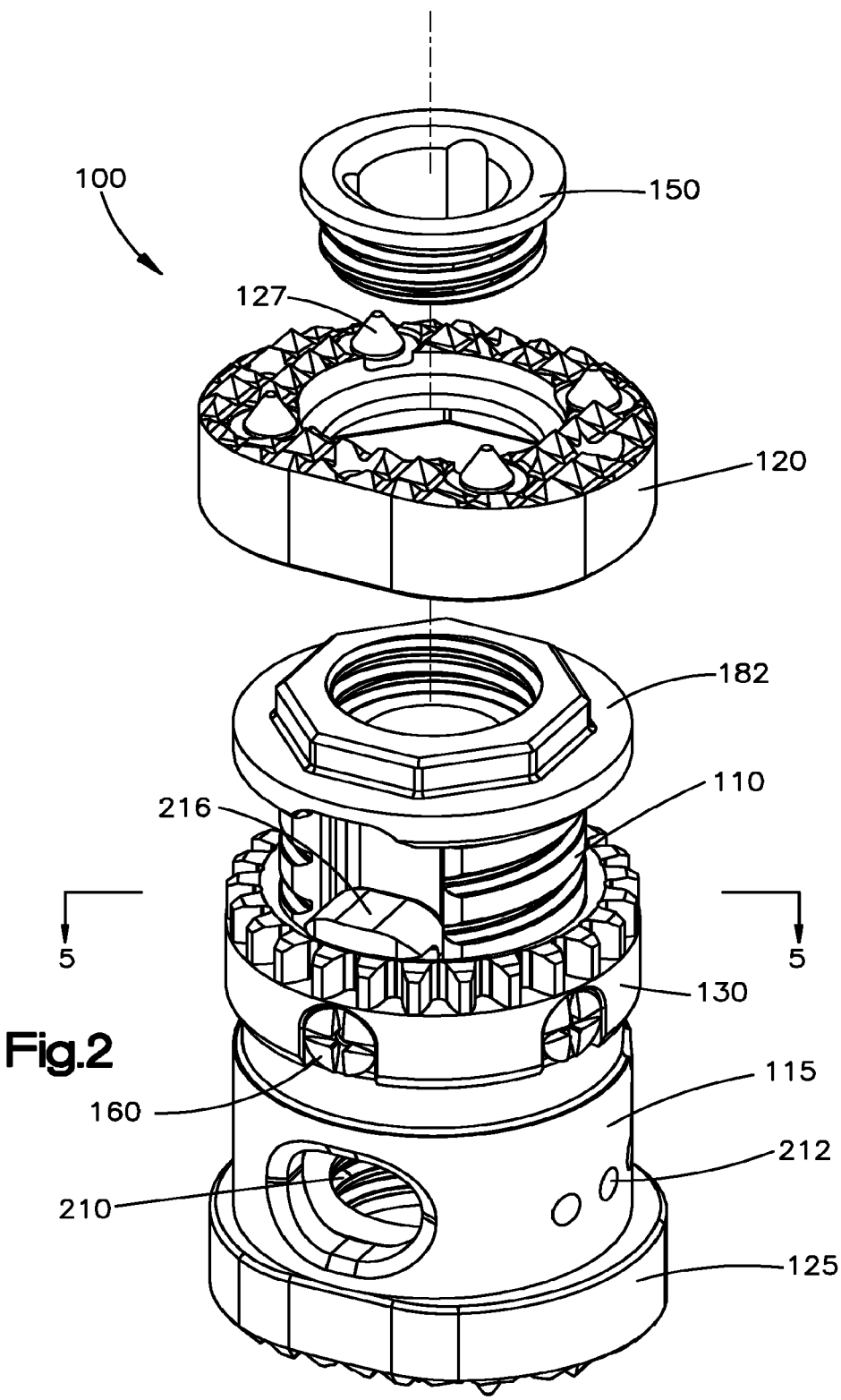
FIG. 2 illustrates a partially exploded front perspective view of the adjustable intervertebral implant of FIG. 1.
Figure 3:
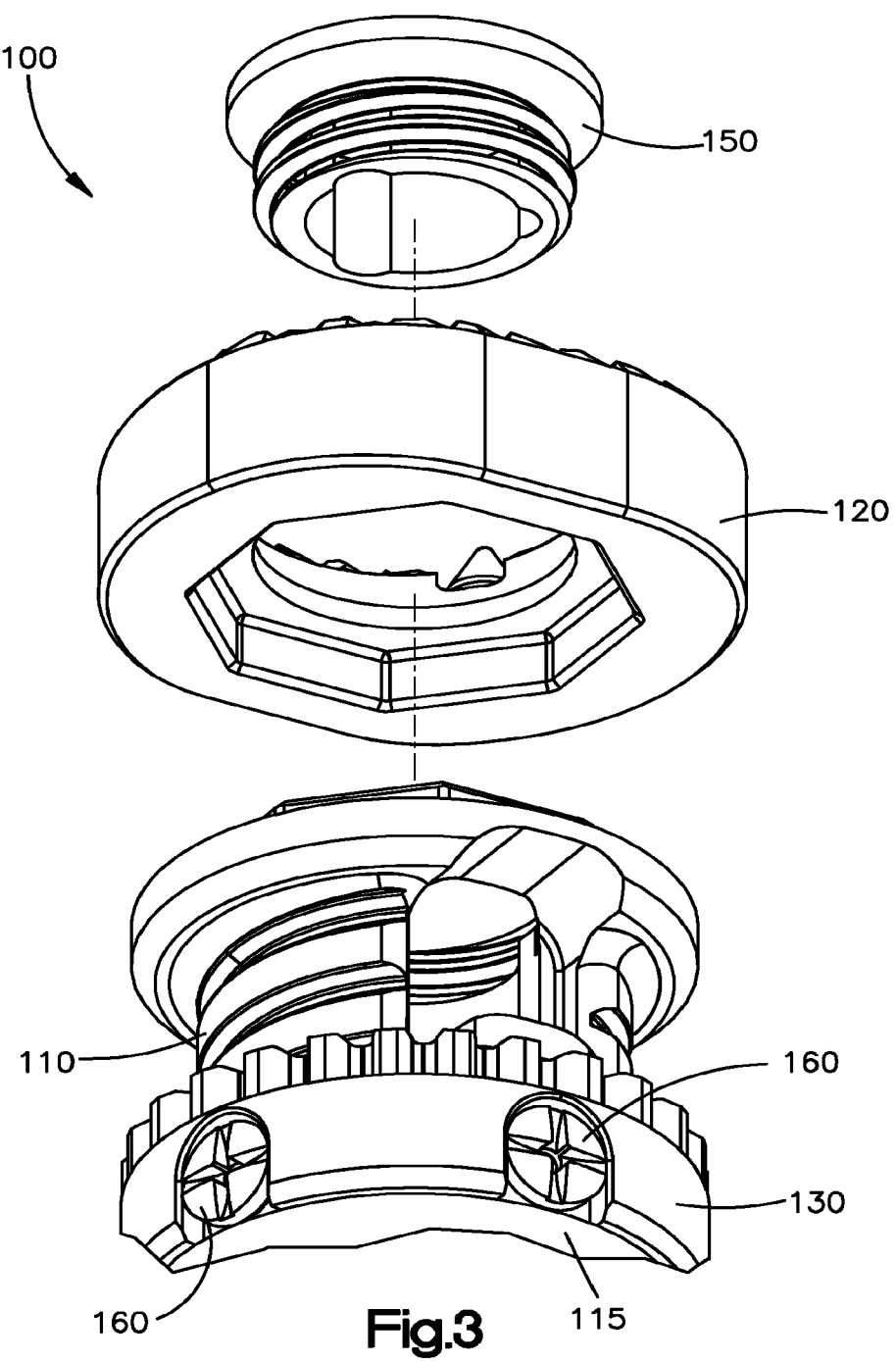
FIG. 3 illustrates a magnified, partially exploded front perspective view of the adjustable intervertebral implant of FIG. 1.
Figure 5:
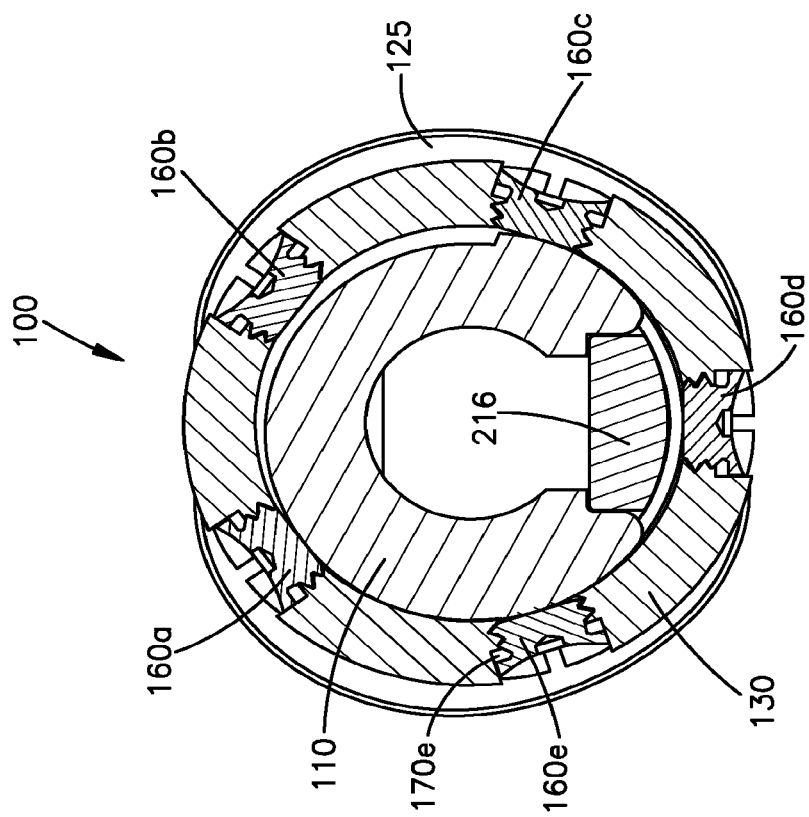
FIG. 5 illustrates a cross-sectional view of the adjustable intervertebral implant of FIG. 1, taken along line 5-5 of FIG. 2.

As best shown in FIGS. 1-3, the inner member 110 may include a superior endplate 120, preferably, detachably coupled to the first end 182 of the inner member 110. Similarly, in the preferred embodiment, an inferior endplate 125 is detachably coupled to the second end 204 of the outer member 115. The superior and inferior end plates 120, 125 are sized and configured for contacting the neighboring vertebral endplates of neighboring vertebrae 50 and are preferably provided in a range of surface geometries to accommodate a range of lordotic or kyphotic angles displayed by the endplates of the neighboring vertebrae 50.

The endplates 120, 125 may be connected to the inner and outer members 110, 115 by any means known in the art, including, but not limited to, interference-fit, threading, screwing, bonding, etc. In this manner, the intervertebral implant 100 can be provided in a kit with a plurality of different endplates 120, 125, thus enabling the user to select the desired endplates 120, 125 that best conform with the contours of the patient's vertebral endplates. By way of example, various endplates 120, 125 may be provided that include varying shapes including, but not limited to, circular, square, rectangular, oval, kidney-shaped, etc. and/or one or more of the following characteristics: a generally wedge-shaped surface, curved surface, flat surface, etc. Alternatively, the upper and lower endplates 120, 125 may be integrally formed with the inner and outer members 110, 115.

Preferably, the superior and inferior end plates 120, 125 are initially coupled to the inner and outer members 110, 115 via a press fit coupling, as is best shown in FIG. 2. The press fit coupling preferably assumes the form of a polygonal interface, illustrated as an octagonal interface, although a range of permissible geometries is envisioned, such that the desired lordotic/kyphotic taper(s) chosen for the superior and inferior endplates 120, 125 can be quickly and removably coupled to the adjustable intervertebral implant 100, regardless of surgical approach (e.g., lateral, posterolateral, anterior, posterior, etc.). For instance, an octagonal coupling interface enables the chosen superior and inferior endplates 120, 125 to be coupled to the adjustable intervertebral implant 100 in forty-five degree (45°) increments with respect to the longitudinal axis 101 such that any desired approach to the spine is permitted. Once the desired lordotic angles of the superior and inferior endplates 120, 125 are chosen and the endplates 120, 125 are press fit to the inner and outer members 110, 115, the endplates 120, 125 are secured to the inner and outer members 110, 115 using optional endplate caps 150, 155, which preferably, threadingly engage a mating thread 151, 156, respectively, internal to the inner and outer members 110, 115.

The surfaces of the superior and inferior endplates 120, 125 include, in a preferred embodiment, anti-expulsion features 127 such as teeth, spikes, ridges, or other surface texturing.

Referring to FIGS. 4, 5 and 8A-9, one or more preloaded set screws 160 is preferably provided to selectively lock the height of the adjustable intervertebral implant 100. Each set screw 160 preferably includes a threaded shaft 162 and a head 164 having a diameter larger than that of the threaded shaft 162. In the preferred embodiment, a plurality, preferably five, set screws 160a-160e are disposed within throughslots 170a-170e that are incrementally spaced around the external surface of the expansion ring 130. The throughslots 170a-170e thereby defining throughslot angles centered on the longitudinal axis 101, the throughslot angles being approximately seventy-two degrees (72°). The throughslots 170, as best shown in FIG. 8A, are characterized by having a proximal portion 172 for housing the head 164 of the set screw 160 and a distal portion 174 for housing the shaft 162 of the set screw 160. The diameter of the proximal portion 172 is preferably larger than the diameter of the distal portion 174. The diameter of the proximal portion 172 of the throughslot 170 is preferably slightly smaller than the diameter that characterizes the head 164 of the set screw 160. Due to the geometry of the throughslots 170, preferably two points of contact exist between the head 164 of the set screw 160 and the proximal portion 172 of the throughslot 170, such that the set screw 160 is retained within the throughslot 170 regardless of whether the set screw 160 has been tighten. As such, the head 164 of each set screw 160 resists rotation and translation of the set screw 160 during implant loading, vibration, shipping and handling, or other sources not introduced by the appropriate instrument, e.g., a screwdriver, thereby enabling the set screws 160 to be preloaded into the expansion ring 130.

In a preferred embodiment, the adjustable intervertebral implant 100 is provided with the plurality of set screws 160 preloaded or already secured within the plurality of through slots 170 at a depth sufficient to enable the expansion ring 130 to be freely rotated and provide a desired construct height while still insuring the secure coupling of the set screws 160 within the throughslots 170 due to the interference therebetween. The advancement of any one of the set screws 160 via an appropriate instrument causes the distal end 165 of the rotationally advanced set screw 160 to bear against the outer surface 186 of the inner member 110 and prevent the expansion ring 130 from further rotation, thereby locking the height of the adjustable intervertebral implant 100. Preferably, in use, a surgeon needs only advance any one conveniently accessible set screw 160 to lock the position of the expansion ring 130 and thus the height of the adjustable intervertebral implant 100. The secure coupling of the preloaded set screws 160 to the expansion ring 130, which is provided by the interference between the head 164 of the set screws 160 and the proximal portion 172 of the throughslots 170, enables the set screws 160 to be preassembled into the expansion ring 130 and securely retained therein, thereby eliminating the extra step of inserting one or more set screws 160 in an appropriate one of the throughslots 170 during surgery and avoiding potential loss of the relatively small set screws 160.

While the interference between the head 164 of the set screw 160 and the proximal portion 172 of the throughslot 170 has been described as being characterized by two points of contact therebetween, it is envisioned that a similar degree of interference can be provided by a range of different interference geometries, such as one or more points of contact, or entire or partial surface area contact between the head 164 of the set screw 160 and the proximal portion 172 of the throughslot 170. Due to the strength of coupling between the head 164 of the set screw 160 and the proximal portion 172 of the throughslot 170 provided by the interference therebetween, it is envisioned that other applications may gain benefit from similarly preloaded set screws under interference, such as transconnectors serving as "ladder rungs" between parallel-implanted spinal rods, wherein the set screw includes a beveled distal end that bears against a spinal rod and urges the spinal rod laterally into a rod-retaining receiving portion of the transconnector, such that the extra step of inserting the relatively small set screw into the transconnector is eliminated and the likelihood of surgical complications (e.g., losing or dropping the tiny set screw) is reduced.

Figure 10:
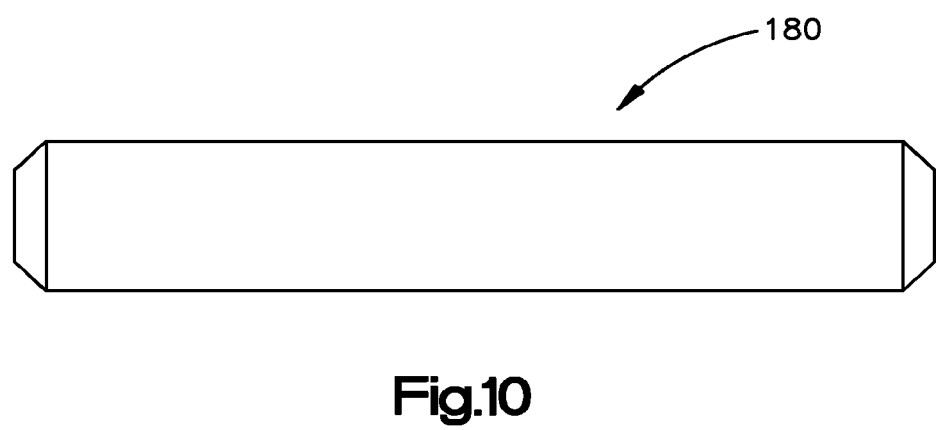
FIG. 10 illustrates a side elevational view of a pin of the adjustable intervertebral implant of FIG. 1.
Figure 11:
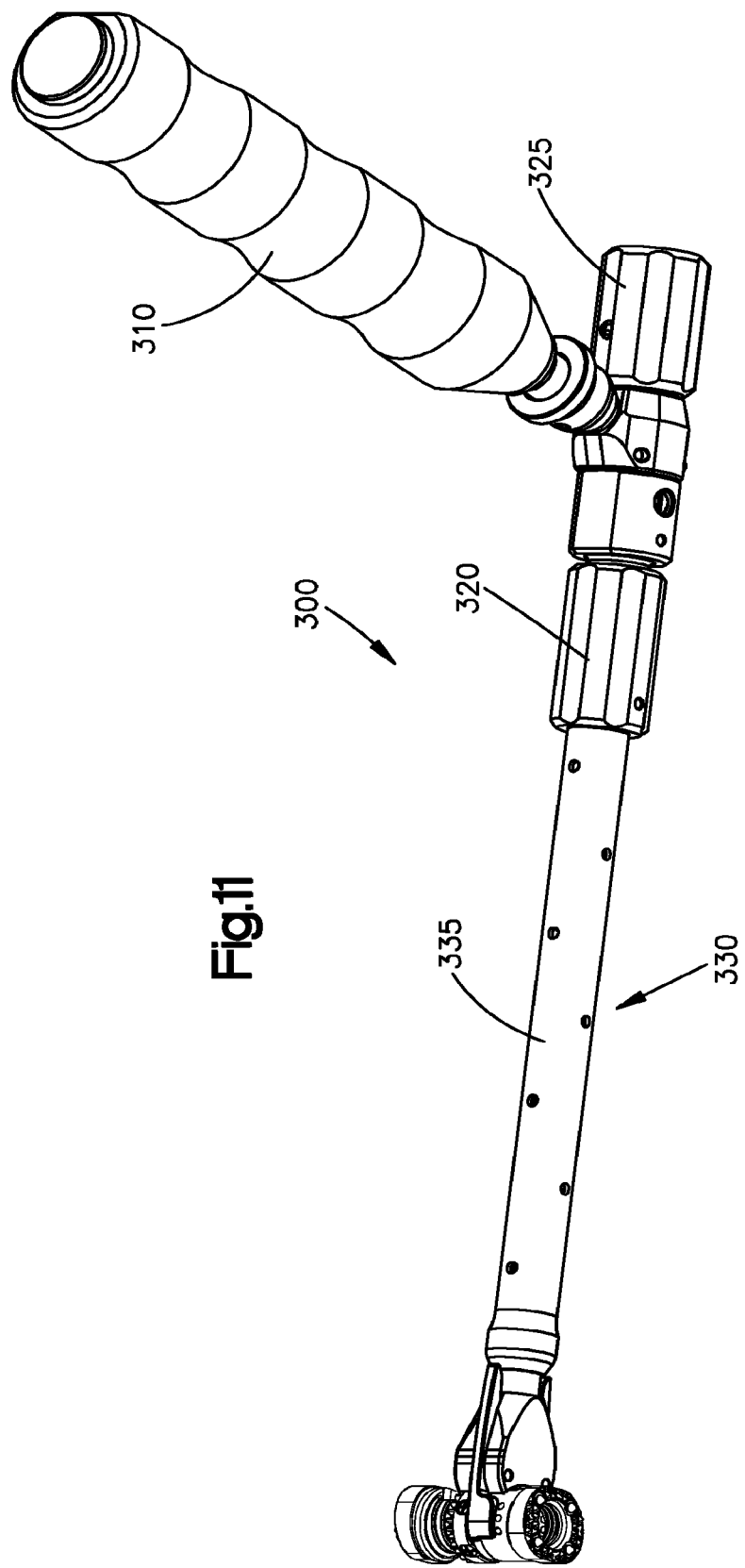
FIG. 11 illustrates a bottom perspective view of the adjustable intervertebral implant of FIG. 1 coupled to an insertion instrument in accordance with a preferred embodiment of the present invention.
Figure 12:
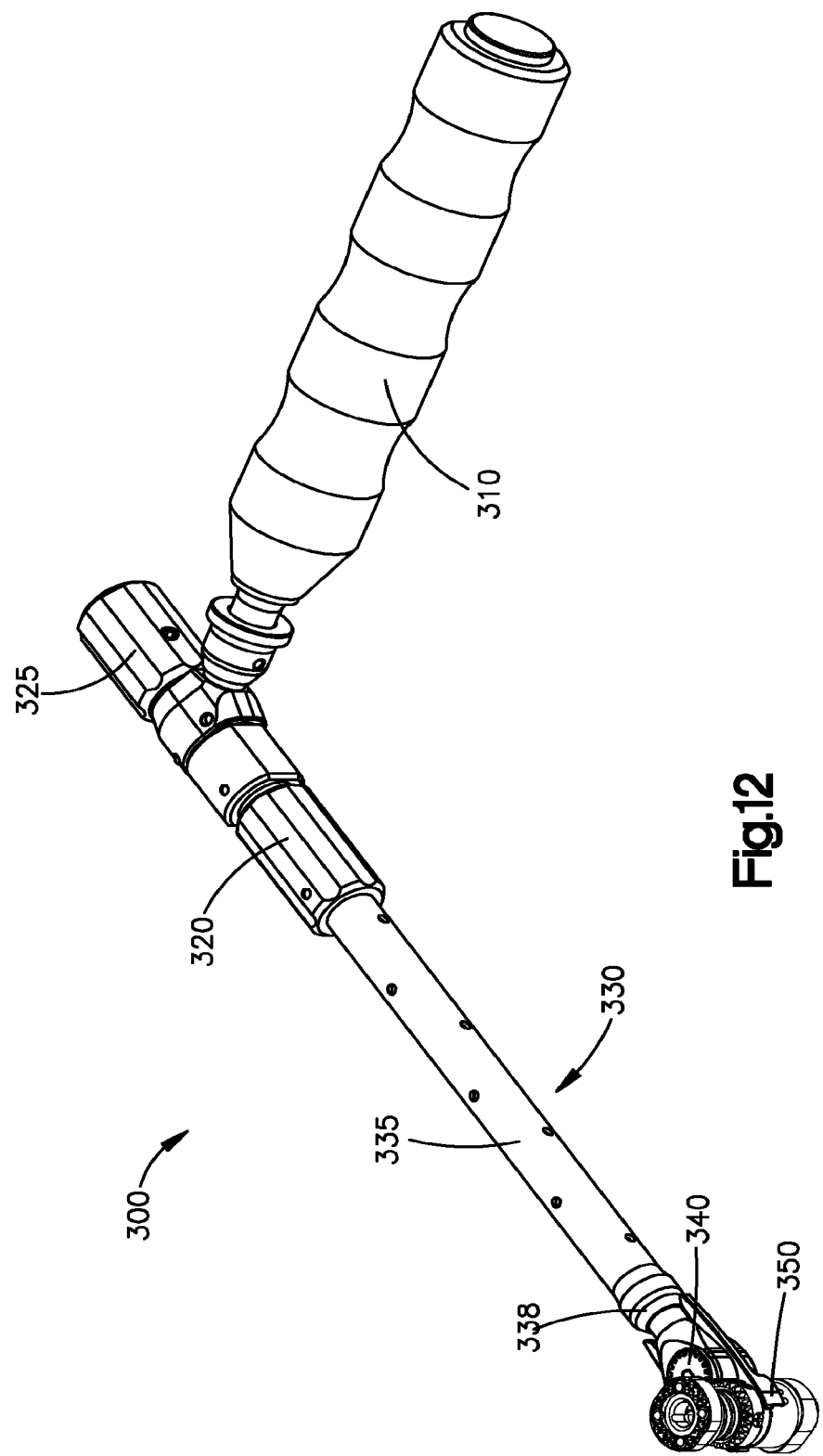
FIG. 12 illustrates a side perspective view of the adjustable intervertebral implant of FIG. 1 coupled to the insertion instrument of FIG. 11.

Referring to FIGS. 1-4, 6C, 6D and 10, the adjustable intervertebral implant 100 preferably also incorporates a pin 180. The pin 180 is preferably disposed within a bore 194 formed in the inner member 110 near the second end 184 of the inner member 110. The pin 180 is preferably constructed of a dense radiographically imagable material such as Titanium-Aluminum-Niobium (TAN). In a preferred embodiment, as best shown in FIGS. 6D and 10, the pin 180 is an elongated cylinder that is disposed generally perpendicular to the longitudinal axis 101 of the inner member 110 so as to be parallel to the radial axis of the expansion ring 130 such that, when the adjustable intervertebral implant 100 is implanted and viewed radiographically, a surgeon can gauge how much expansion has taken place and how much expansion is still afforded by the adjustable intervertebral implant 100 by viewing the longitudinal axis of the pin 180 with respect to the parallel disposed radiographically visible image of the expansion ring 130. When the adjustable intervertebral implant 100 is fully expanded, the pin 180 is preferably positioned close to or may be occluded by the expansion ring 130.

Figure 13:
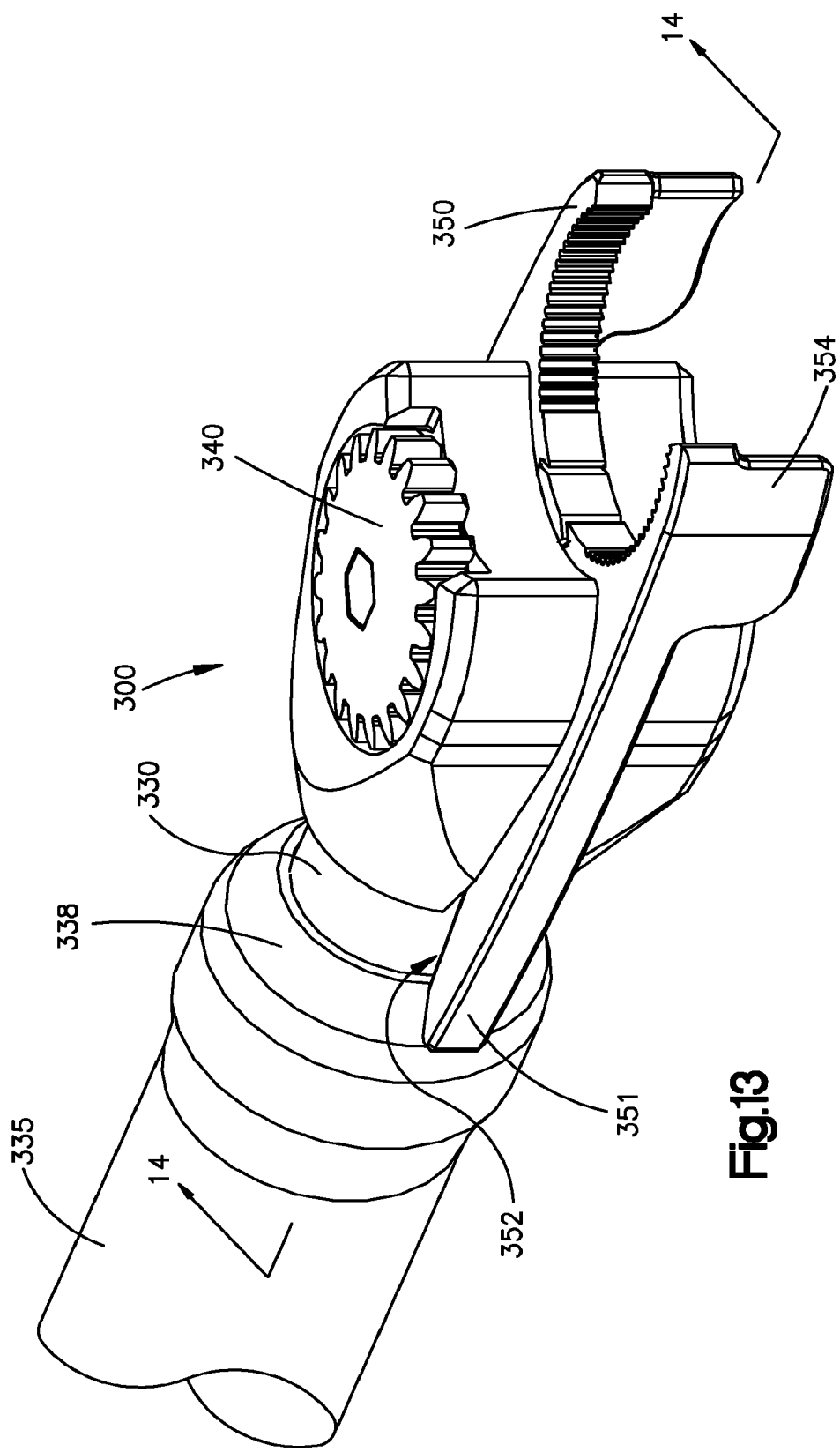
FIG. 13 illustrates a magnified top perspective view of a grasping end of the insertion instrument of FIG. 11.
Figure 14:
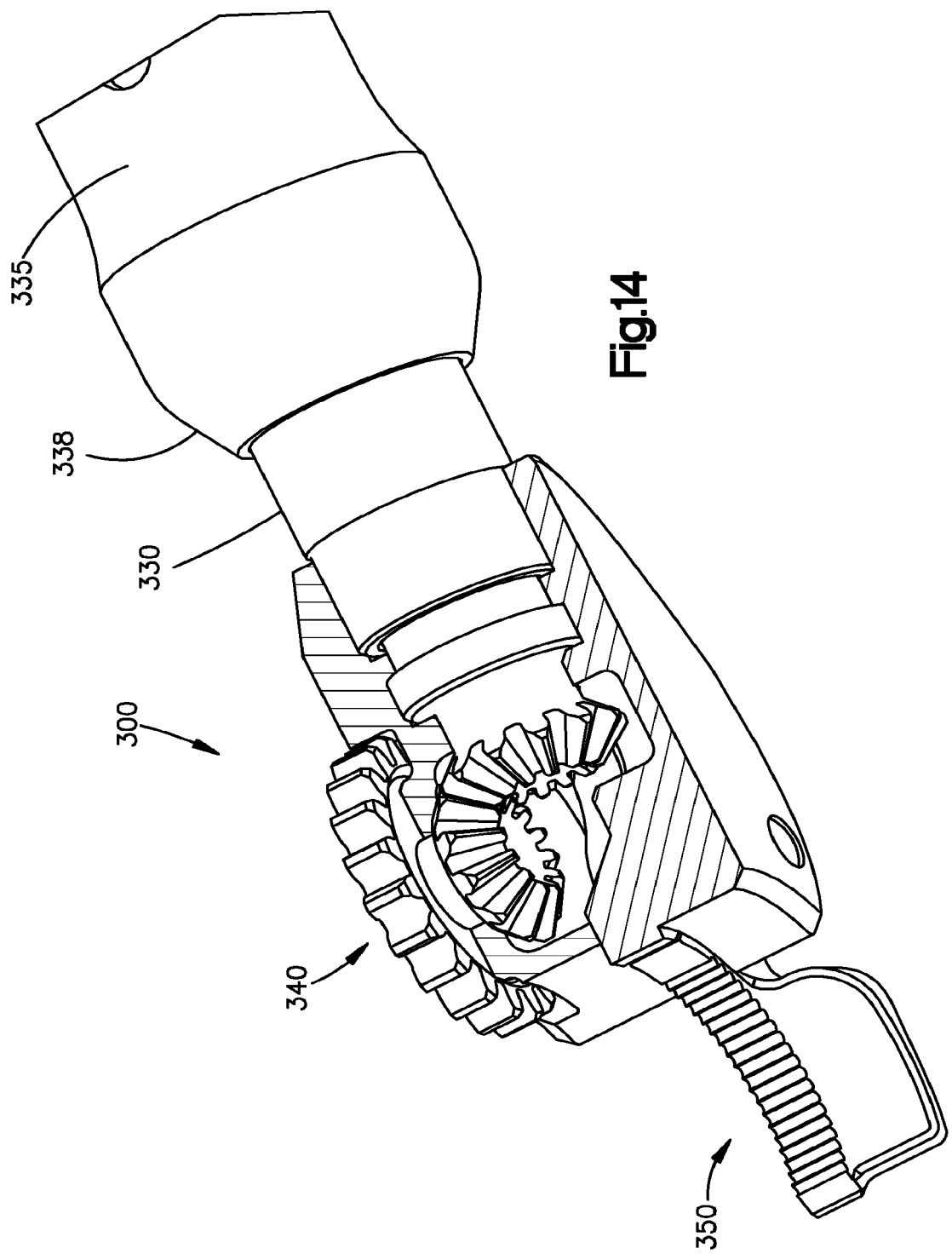
FIG. 14 illustrates a partial cross-sectional view of the insertion instrument of FIG. 11, taken along line 14-14 of FIG. 13 and showing details of gears of the insertion instrument.

Referring to FIGS. 11-14, an expansion and insertion instrument 300 is provided for use with the adjustable intervertebral implant 100. The expansion and insertion instrument 300 includes a handle 310, a shaft 330 and a translatable sleeve 335 disposed around the shaft 330. The sleeve 335 further includes a distally tapered end 338. Disposed along the proximal portion of the shaft 330 are a first manipulating mechanism 320 and a second manipulating mechanism 325. Disposed near the distal end of the shaft 330 is a pair of grasping claws 350 and a gear 340. Actuation, preferably rotation, of the first manipulation mechanism 320 causes one or both of the grasping claws 350 to open and/or close to enable the grasping claws 350 to surround the outer member 115 or to release the outer member 115. In the preferred embodiment, as best shown in FIG. 13, rotation of the first manipulating mechanism 320 forces the sleeve 335 to translate distally along the shaft 330 and causes the distal taper 338 to engage the interior surface 352 of the proximal portion 351 of the grasping claws 350, thereby pivoting the grasping claws 350 closed about a pivot point provided by a pin that secures the grasping claws 350 to the expansion and insertion instrument 300. That is, in use, initially, the grasping claws 350 are opened so that the grasping claws 350 can surround the outer member 115. The first manipulating mechanism 320 is then actuated, e.g., rotated, to translate the sleeve 335 distally along the shaft 330 to thereby engage the mating surfaces of the interior of the proximal end of the grasping claws 350 and the distal taper 338 of the sleeve 335, thereby causing the interior surface of the grasping claws 350 to firmly grasp the outer member 115.

In the preferred embodiment, the outer member 115 includes one or more instrument engagement features, which may be in the form of indentations or grooves, that mate with the interior surface of the distal end 354 of the grasping claws 350 or alternative surface features thereupon. When the adjustable intervertebral implant 100 is securely coupled to the expansion and insertion instrument 300 via the grasping claws 350, the gear 340 functionally contacts the series of teeth 134 formed on the outer surface of the expansion ring 130. Actuation, preferably rotation, of the second manipulating mechanism 325 causes the gear 340 to rotate and, in turn, causes the expansion ring 130 to rotate with respect to the adjustable intervertebral implant 100, which in turn causes telescopic expansion or contraction of the adjustable intervertebral implant 100, depending on the direction of rotation.

In operation, the adjustable intervertebral implant 100 may optionally be filled by the surgeon with bone graft material within its axial bore to allow fusion between the neighboring vertebral endplates of the neighboring vertebrae 50 and through the adjustable intervertebral implant 100. A surgeon elects the desired lordotic taper for the superior and inferior endplates 120, 125 and press fits the superior and inferior endplates 120, 125 to the inner and outer members 110, 115, respectively, at any one of several positions, depending on the elected surgical access path provided by the polygonal interface therebetween. The surgeon then preferably chooses to secure the endplates 120, 125 to the adjustable intervertebral implant 100 using the superior and inferior endplate caps 150, 155. The adjustable intervertebral implant 100 is engaged with the insertion and expansion instrument 300 using the grasping claws 350 via the actuation of the first manipulation mechanism 320. The adjustable intervertebral implant 100 is preferably implanted in its lowest height configuration between the neighboring vertebral endplates of the neighboring vertebrae 50 and expands the adjustable intervertebral implant 100 in situ using the second manipulation mechanism 325 while visualizing radiographically the height expansion of the adjustable intervertebral implant 100, taking into account the position of the image of the pin 180 and the image of the expansion ring 130. Once the desired height of the adjustable intervertebral implant 100 is reached, one of the set screws 160 is advanced using a simple instrument, such as a screwdriver, to lock the height of the adjustable intervertebral implant 100.

While the foregoing description and drawings represent the preferred embodiment of the present invention, it will be understood that various additions, modifications, combinations and/or substitutions may be made therein without departing from the spirit and scope of the invention as defined in the accompanying claims. In particular, it will be apparent to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. The presently disclosed embodiments are, therefore, to be considered in all respects as illustrative and not restrictive, the scope of the invention being indicated by the appended claims, and not limited to the foregoing description.

We claim:

1. An adjustable intervertebral implant for implanting between neighboring vertebral bodies to replace all or a significant portion of a damaged vertebra, the adjustable intervertebral implant comprising:
    a radiolucent inner member having a longitudinal axis extending between a first end and a second end, a throughslot extending from the second end of the inner member along the longitudinal axis of the inner member, a first threading on an outer surface of the inner member;
    a radiolucent outer member having a longitudinal axis extending between a first end and a second end, the inner member slidably received within a bore provided within the outer member between the first and second end of the outer member, the inner member slidably movable within the bore in a direction along the longitudinal axis of the outer member;
    a radiographically visible expansion ring having inner and outer surfaces, the inner surface having a second threading thereon, wherein a width of crests of the first threading is greater than a width of crests of the second threading, the expansion ring being rotatably coupled to the outer member so that rotation of the expansion ring results in engagement of the first and second threadings and slidable translation of the inner member with respect to the outer member, the expansion ring further including a plurality of unthreaded throughslots disposed circumferentially around the expansion ring; and
    at least one set screw wherein advancement of one of the at least one set screw within a corresponding one of the plurality of unthreaded throughslots causes a distal end of the one of the at least one set screw to bear against the outer surface of the inner member and thereby secure the inner member relative to the outer member in a locked position.

2. An adjustable intervertebral implant for implanting between adjacent vertebrae bodies to replace all or a significant portion of a damaged vertebra, the adjustable intervertebral implant comprising:
    an inner member having a longitudinal axis extending between a first end and a second end, a throughslot defining an elongated opening in a sidewall of the inner member extending from the second end of the inner member along the longitudinal axis of the inner member, a first threading on an outer surface of the inner member;
    an outer member having a longitudinal axis extending between a first end and a second end, a tab protruding axially beyond the first end of the outer member and terminating in a lip protruding from a distal end of the tab, the inner member slidably received within a bore provided within the outer member between the first and second ends of the outer member, the inner member slidably movable within the bore in a direction along the longitudinal axis of the outer member, the slidable movement guided by interaction of the tab with the throughslot formed in the inner member, wherein a diameter of the inner member at a crest of the first threading is less than a diameter of the bore of the outer member;
    an expansion ring having an inner surface provided with a second threading thereon, the expansion ring received around the tab protruding beyond the outer member and below the lip so as to be freely rotatable with respect to the outer member, the expansion ring further including an unthreaded throughslot; and
    a pre-loaded set screw having a head and a threaded shaft, the head of the set screw positioned within a proximal portion of the unthreaded throughslot by an interference fit,
    wherein actuation of the expansion ring results in engagement of the first and second threadings and slidable translation of the inner member with respect to the outer member,
    wherein advancement of the set screw within the unthreaded throughslot causes a distal end of the set screw to bear against the outer surface of the inner member and thereby secure the inner member relative to the outer member in a locked position.

3. The adjustable intervertebral implant of claim 2, further comprising:
    a first coupling interface at the first end of the inner member;
    a second coupling interface at the second end of the outer member; and
    detachable superior and inferior endplates each having a coupling interface for attachment to the first coupling interface and the second coupling interface of the inner member and the outer member, respectively.

4. The adjustable intervertebral implant of claim 3, further comprising:
    a superior endplate cap for coupling the superior endplate to the first coupling interface, the superior endplate cap threadably engaging a threaded bore provided within the inner member; and
    an inferior endplate cap for coupling the inferior endplate to the second coupling interface, wherein threads provided on the threaded bore of the inner member extend within the threaded bore at least an axial length corresponding to an axial length of the first coupling interface, wherein threads provided on the bore of the outer member extend within the bore at least an axial length corresponding to an axial length of the second coupling interface, wherein the coupling interfaces are each comprised of a polygonal coupling interface having a shape of a polygon, allowing each endplate to be coupled to a respective one of the inner and outer members at any number of positions that correspond to a number of sides of the polygon.

5. The adjustable intervertebral implant of claim 3, wherein at least one of the superior or inferior endplates includes a lordotic or kyphotic taper.

6. The adjustable intervertebral implant of claim 2, further comprising:

a radiographically imagable marker disposed within the inner member.

7. The adjustable intervertebral implant of claim 6, wherein the radiographically imagable marker is comprised of a pin mounted proximate the second end of the inner member.

8. The adjustable intervertebral implant of claim 7, wherein the pin includes a pin axis, the pin axis oriented generally perpendicular to the longitudinal axis of the inner member.

9. The adjustable intervertebral implant of claim 2, wherein the distal end of the pre-loaded set screw engages a planar apex of the first threading of the inner member in the locked position.

10. The adjustable intervertebral implant of claim 2, wherein the second end of the inner member is positioned proximate the second end of the outer member and the first end of the inner member is positioned proximate the first end of the outer member in a loading position, the second end of the inner member positioned proximate the first end of the outer member in a fully expanded position.

11. The adjustable intervertebral implant of claim 10, further comprising:

a radiographically imagable pin mounted proximate the second end of the inner member.

12. The adjustable intervertebral implant of claim 2, wherein the unthreaded throughslot includes a plurality of unthreaded throughslots disposed circumferentially around the expansion ring, each of the plurality of unthreaded throughslots characterized by a proximal portion and a distal portion, wherein the proximal portion of each of the plurality of unthreaded throughslots is characterized by a diameter larger than a diameter of the distal portion of each of the plurality of unthreaded throughslots, and wherein the unthreaded throughslots are evenly spaced circumferentially around the expansion ring, thereby defining throughslot angles centered on the longitudinal axis.

13. The adjustable intervertebral implant of claim 12, wherein the pre-loaded set screw includes a plurality of pre-loaded set screws, each of the plurality of pre-loaded set screws having a head and a threaded shaft, the head of each of the plurality of pre-loaded set screws positioned within the proximal portion of a corresponding one of the unthreaded throughslots by an interference fit, wherein advancement of any one of the plurality of pre-loaded set screws within the corresponding one of the plurality of unthreaded throughslots causes a distal end of the one of the plurality of pre-loaded set screws to bear against the outer surface of the inner member and thereby secure the inner member relative to the outer member in a locked position.

14. The adjustable intervertebral implant of claim 13, wherein the plurality of pre-loaded set screws is comprised of five (5) pre-loaded set screws.

15. The adjustable intervertebral implant of claim 2, wherein the outer member includes an instrument engagement feature.

16. The adjustable intervertebral implant of claim 2, wherein a first coupling interface of the inner member and a second coupling interface of the outer member have an octagonal shape.

17. The adjustable intervertebral implant of claim 2, wherein the expansion ring includes an instrument engagement feature.

18. The adjustable intervertebral implant of claim 17, wherein the instrument engagement feature of the expansion ring includes a series of teeth located circumferentially around an exterior of the expansion ring.

19. The adjustable intervertebral implant of claim 2, wherein a width of crests of the first threading is greater than a width of crests of the second threading.

20. An adjustable intervertebral implant for implanting between adjacent vertebrae bodies to replace all or a significant portion of a damaged vertebra, the adjustable intervertebral implant comprising:

an inner member having a longitudinal axis extending between a first end and a second end, a throughslot extending from the second end of the inner member along the longitudinal axis of the inner member, a first threading on an outer surface of the inner member;

an outer member having a longitudinal axis extending between a first end and a second end, a tab protruding axially beyond the first end of the outer member along the longitudinal axis of the outer member and terminating in a lip, the inner member slidably received within a bore provided within the outer member between the first and second ends of the outer member, the inner member slidably movable within the bore in a direction along the longitudinal axis of the outer member, the slidable movement guided by interaction of the tab with the throughslot formed in the inner member, wherein a diameter of the inner member at a crest of the first threading is less than a diameter of the bore of the outer member;

an expansion ring having an inner surface provided with a second threading thereon, the expansion ring received around the tab protruding beyond the outer member and below the lip so as to be freely rotatable with respect to the outer member, rotation of the expansion ring resulting in engagement of the first and second threadings and translation of the inner member with respect to the outer member, the expansion ring further including a plurality of unthreaded throughslots disposed circumferentially around the expansion ring; and at least one set screw, each of the at least one set screw having a head and a threaded shaft, wherein advancement of one of the at least one set screw within a corresponding one of the plurality of unthreaded throughslots causes a distal end of the one of the at least one set screw to bear against the outer surface of the inner member and thereby secure the inner member relative to the outer member in a locked position.

\* \* \* \* \*